(12) United States Patent
Lee et al.

(10) Patent No.: US 6,430,427 B1
(45) Date of Patent: Aug. 6, 2002

(54) METHOD FOR OBTAINING TRABECULAR INDEX USING TRABECULAR PATTERN AND METHOD FOR ESTIMATING BONE MINERAL DENSITY USING TRABECULAR INDICES

(75) Inventors: Soo-Yeul Lee; Seon-Hee Park; Seung-Hwan Kim; Hyeon-Bong Pyo, all of Taejon (KR)

(73) Assignee: Electronics and Telecommunications Research Institute (KR)

( * ) Notice: Subject to any disclaimer, the term of this patent is extended or adjusted under 35 U.S.C. 154(b) by 0 days.

(21) Appl. No.: 09/371,264

(22) Filed: Aug. 10, 1999

(30) Foreign Application Priority Data

Feb. 25, 1999 (KR) .............................. 99-6279
Jun. 11, 1999 (KR) ............................. 99-21703

(51) Int. Cl.[7] ................................ A61B 5/05
(52) U.S. Cl. ..................... 600/407; 382/128
(58) Field of Search .................. 600/407, 436, 600/408; 382/128, 131, 132, 133, 168, 169, 170, 171, 172, 173; 378/54

(56) References Cited

U.S. PATENT DOCUMENTS

| | | | | |
|---|---|---|---|---|
| 4,829,549 A | * | 5/1989 | Vogel et al. .................. | 378/55 |
| 4,903,203 A | * | 2/1990 | Yamashita et al. ...... | 364/413.15 |
| 4,922,915 A | * | 5/1990 | Arnold et al. ............... | 128/653 |
| 5,247,934 A | * | 9/1993 | Wehrli et al. ............... | 600/410 |
| 5,915,036 A | * | 6/1999 | Grunkin et al. ............. | 382/132 |
| 5,931,780 A | * | 8/1999 | Giger et al. ................ | 600/407 |
| 6,021,213 A | * | 2/2000 | Helterbrand et al. ........ | 382/128 |
| 6,205,348 B1 | * | 3/2001 | Giger et al. ................ | 600/407 |
| 6,246,784 B1 | * | 6/2001 | Summers et al. ........... | 382/128 |
| 6,249,594 B1 | * | 6/2001 | Hibbard ...................... | 382/128 |
| 6,310,967 B1 | * | 10/2001 | Heine et al. ................. | 382/128 |
| 6,332,034 B1 | * | 12/2001 | Makram-Ebeid et al. ... | 382/128 |
| 6,345,112 B1 | * | 2/2002 | Summers et al. ........... | 382/128 |

\* cited by examiner

*Primary Examiner*—Marvin M. Lateef
*Assistant Examiner*—Eleni Mantis Mercader
(74) *Attorney, Agent, or Firm*—Blakely Sokoloff Taylor & Zafman

(57) ABSTRACT

A method for obtaining a trabecular index using a trabecular pattern displayed on an X-ray image and a method for estimating a bone mineral density using trabecular indices are disclosed. The method for obtaining the trabecular index analyzes trabecular pattern changes, due to decalcifications of trabeculae, displayed on the X-ray picture and quantifies the changes, thereby obtaining the trabecular index. The method for estimating the bone mineral density obtains trabecular indices and then estimates the bone mineral density corresponding to the trabecular index using a functional relation between the trabecular index and actual bone mineral density.

20 Claims, 4 Drawing Sheets

METHOD FOR OBTAINING TRABECULAR INDEX USING TRABECULAR PATTERN AND METHOD FOR ESTIMATING BONE MINERAL DENSITY USING TRABECULAR INDICES

FIELD OF THE INVENTION

The present invention relates to a method for obtaining a trabecular index using a trabecular pattern and a method for estimating a bone mineral density using trabecular indices.

DESCRIPTION OF THE PRIOR ART

Osteoporosis is a wide spread medical condition that affects the middle-aged and older populations. Especially, the condition is prevalent in postmenopausal women. Osteoporosis is characterized by an abnormal loss in bone mineral content, which leads to a tendency toward non-traumatic bone fractures and to structural deformations of bones. However, effective therapy for osteoporosis has not been developed yet. Only several methods for reducing the occurrence possibility of osteoporosis through physical exercises or appropriate diets are known. Accordingly, it is important that a method for easily and inexpensively diagnosing the osteoporosis should be developed for the prevention of deterioration of osteoporosis and early stage treatment of osteoporosis.

Bone mineral density measurement is basic for diagnosing osteoporosis because osteoporosis is characterized by an abnormal loss in bone mineral content. Various methods have been developed for the quantitative measurement of bone mineral density. The most widely used method for measuring bone mineral density is dual photon absorptiometry with either an X-ray or nuclear source. The accuracy error of this method in determining bone mineral content is reported to be about few percentages. Quantitative computed tomography provides a three-dimensional bone density assessment and separate estimations of cortical and trabecular bone densities. However, the routine use of these bone densitometries is precluded by their high costs.

Mechanical strength of the whole bone is determined mainly by the dense cortical part. However, many investigators have indicated that the trabecular bone is also an important factor in determining mechanical strength of bone. Moreover, it is well known that the trabecular bone is resorbed more rapidly than cortical bone in osteoporosis. This implies that the trabecular bone is more reflective of the stage of osteoporosis and that early stage intervention in osteoporosis can be possible through an evaluation of changes in trabecular bone. In this sense, many investigators have studied trabecular patterns appearing on conventional X-ray images. As clinical tools for assessing changes in trabecular patterns of X-ray images, Saville's and Singh's indices are available. These indices assess stages of osteoporosis using trabecular patterns changes appearing on X-ray images of the lateral lumbar spine and the upper part of the femur. In computerized image processing approach, various textural measures such as gray level statistics, frequency domain analysis, and fractal dimension analysis have been applied to quantify changes of trabecular pattern. These methods are reported to be somewhat successful to anticipate fracture risks of bone. But they do not provide trabecular indices well correlated with quantitative bone mineral density.

SUMMARY OF THE INVENTION

It is, therefore, an object of the present invention to provide a method for obtaining a trabecular index using a trabecular pattern of an X-ray image and a computer-readable medium for performing the method.

It is another object of the present invention to provide a method for obtaining a trabecular index by quantifying changes in a trabecular pattern appearing on an X-ray image and a computer-readable medium for performing the method.

It is further another object of the present invention to provide a method for estimating a bone mineral density using trabecular indices and a computer-readable medium for performing the method.

In accordance with an aspect of the present invention, there is provided a method for obtaining a trabecular index using a trabecular pattern in a computer, comprising the steps of: (a) obtaining an X-ray image of a bone; (b) determining a region of interest on the X-ray image; (c) dividing the region of interest into a plurality of blocks including a plurality of pixels; (d) calculating a gray level of each pixel; (e) scaling gray levels of the pixels for each block with a linear function; (f) calculating an average gray level of each block; and (g) obtaining the trabecular index by re-averaging the average gray levels for the blocks.

In accordance with another aspect of the present invention, there is provided a method for estimating a target bone mineral density using a target trabecular index in a computer, comprising the steps of: (a) obtaining X-ray images of sample bones; (b) determining regions of interest on the X-ray images; (c) obtaining a trabecular index corresponding to each region of interest; (d) measuring a bone mineral density of each sample with a bone densitometer; (e) obtaining a functional relation between the trabecular index and the bone mineral density; and (f) estimating the target bone mineral density using the target trabecular index related to a target bone from the functional relation.

In accordance with further another aspect of the present invention, there is provided a computer-readable medium for performing the steps. of: (a) obtaining an X-ray image of a bone; (b) determining a region of interest on the X-ray image; (c) dividing the region of interest into a plurality of blocks including a plurality of pixels; (d) calculating a gray level of each pixel; (e) scaling gray levels of the pixels for each block with a linear function; (f) calculating an average gray level of each block; and (g) obtaining the trabecular index by re-averaging the average gray levels for the blocks.

In accordance with furthermore another aspect of the present invention, there is provided a computer-readable medium for performing the steps of: (a) obtaining X-ray images of sample bones; (b) determining regions of interest on the X-ray images; (c) obtaining a trabecular index corresponding to each region of interest; (d) measuring a bone mineral density of each sample with a bone densitometer; (e) obtaining a functional relation between the trabecular index and the bone mineral density; and (f) estimating a target bone mineral density using a target trabecular index related to a target bone from the functional relation.

BRIEF DESCRIPTION OF THE DRAWINGS

Other objects and aspects of the present invention will become apparent from the following description of the embodiments with reference to the accompanying drawings, in which.

DETAILED DESCRIPTION OF THE INVENTION

Hereafter, the present invention will be described in detail with reference to the accompanying drawings.

Figure 1:
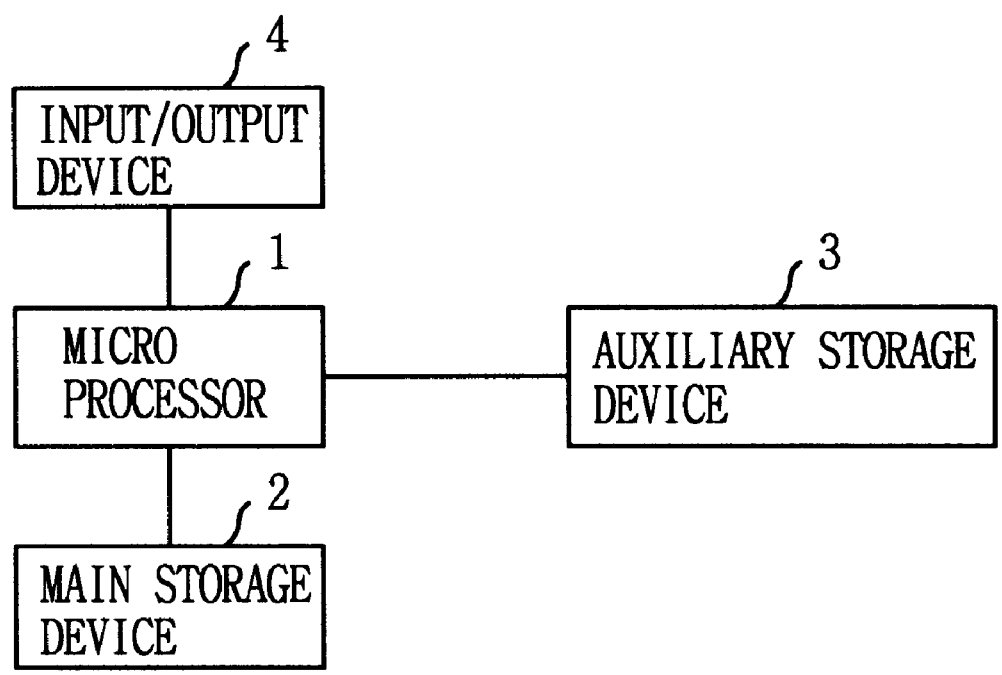
FIG. 1 is a block diagram illustrating a hardware system to which the present invention is applied.

Referring to FIG. 1, a hardware system to which the present invention is applied is basically employed to carry out a process for obtaining a trabecular index of the distal radius using a distal radius trabecular pattern and estimating a bone mineral density of the distal radius. The hardware system includes a microprocessor 1, a main storage device 2, an auxiliary storage device 3 and an input/output device 4. The input/output device 4 receives data from a user and outputs data to the user, and the main and auxiliary storage devices 2 and 3 store data needed to obtain the trabecular index of the distal radius using the trabecular pattern and estimate the bone mineral density of the distal radius using trabecular indices. The microprocessor 1 obtains the trabecular index of the distal radius using the trabecular pattern and estimates the bone mineral density of the distal radius using the trabecular indices, controlling the main and auxiliary storage devices 2 and 3 and the input/output device 4. When the microprocessor 1 including a program receives data of an X-ray image of the wrist and carries out the program, the program obtains the trabecular index of the distal radius using the distal radius trabecular pattern and measures the bone mineral density of the distal radius using trabecular indices.

Figure 2:
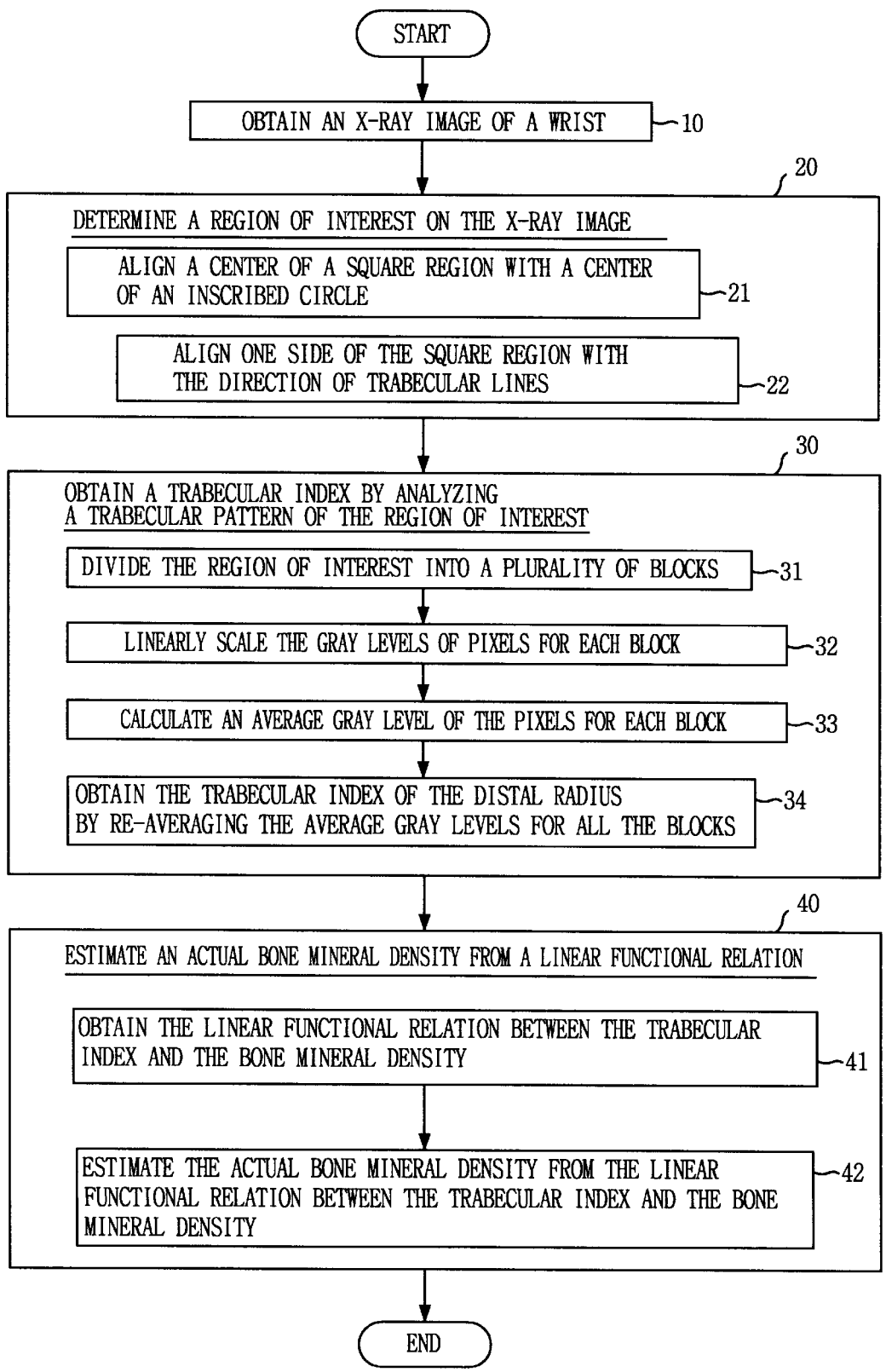
FIG. 2 is a flow chart illustrating a method for obtaining a trabecular index using a trabecular pattern on the X-ray image and a method for estimating a bone mineral density using trabecular indices according to an embodiment of the present invention.

FIG. 2 is a flow chart illustrating a method for obtaining a trabecular index using a trabecular pattern displayed on an X-ray image of a distal radius and a method for estimating a bone mineral density using trabecular indices according to an embodiment of the present invention.

Figure 3:
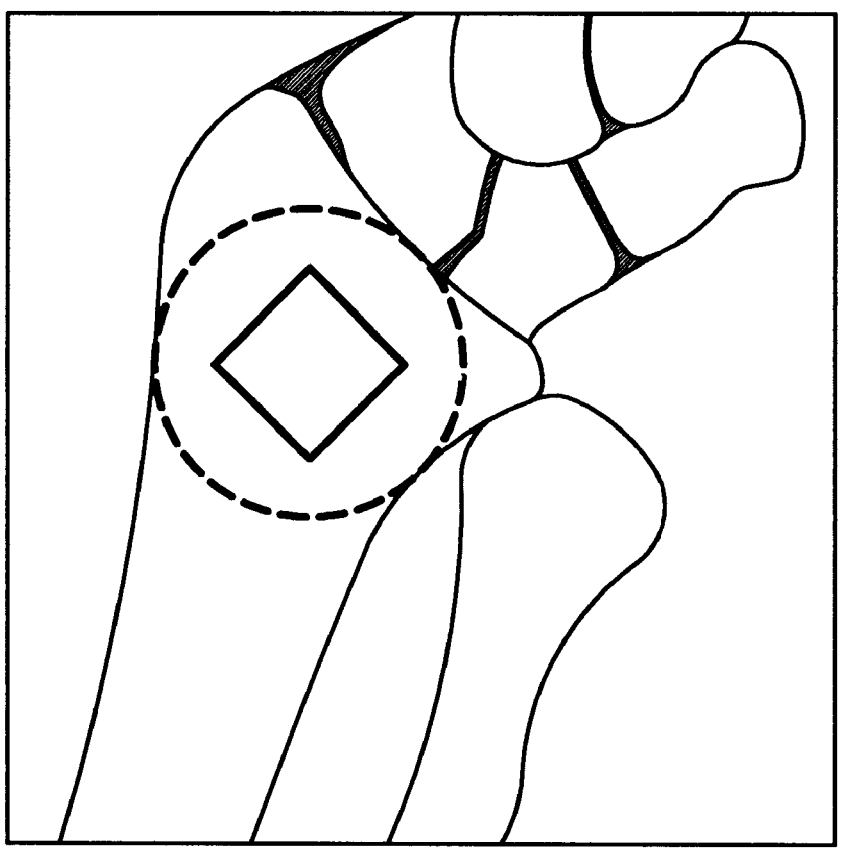
FIG. 3 shows a wrist X-ray image and a region of interest determined to obtain a trabecular index of a distal radius.

Referring to FIG. 2, at step 10, a wrist X-ray image (see FIG. 3) is obtained for a measurement of a distal radius bone mineral density. When a wrist is radiographed, a standard anteroposterior X-ray projection scheme is used and the wrist is adhered closely to a cartridge of the X-ray film. Then, the size of distal radius in the X-ray image may be close to an actual size of distal radius and image blurring of the X-ray image may be minimized. Each pixel of the X-ray image is mapped to a gray level related to the bone mass per unit area. Since the gray level changes according to the X-ray exposure condition and X-ray film development condition, the gray level is not exactly mapped to the bone mineral density. Furthermore, the gray level contains contributions from overlapping soft tissues. Thus the gray level of the X-ray image may not be directly used as a measure of the bone mineral density.

At step 20, a region of interest, which is in the form of a square, is determined on the distal radius of the X-ray image.

At step 21, an inscribed circle is determined on the distal radius part (see FIG. 3) and the center of the square region of interest is aligned with the center of the inscribed circle.

At step 22, one side of the square region of interest is aligned with the direction of main trabecular lines on the distal radius of the X-ray image.

At step 30, a trabecular pattern in the region of interest is analyzed and the trabecular index is obtained by quantifying the change of the trabecular pattern due to decalcification of trabeculae.

At step 31, the region of interest is divided into a plurality of square blocks. The length of the side of the block has a value between 1.0 mm and 1.5 mm. The length of the side of the block is comparable to the average inter-trabecular distance between main trabecular lines displayed on the distal radius of the X-ray image.

At step 32, the gray levels in each block are scaled with a linear function such that the lowest and highest gray levels become 0 and 255, respectively. Once the gray levels in each block are linearly scaled, the image variation caused by changes of the X-ray exposure condition and the X-ray film development condition will be minimized. Furthermore, a background trend existing within the region of interest will be significantly removed.

At step 33, an average gray level in each block is calculated.

At step 34, the average gray levels for all the blocks are re-averaged. Then the trabecular index of the distal radius is defined by this re-averaged value.

The reason why the trabecular index of the distal radius has a meaning as a measure of the bone mineral density is as follows. When the bone mineral density is decreased, trabecular bones are also decalcified at their surfaces. Thus the thickness of the trabecular line in the X-ray image is also decreased. When it is assumed that the linearly scaled gray level in the block corresponds to a height in the three-dimensional topography, the trabecular line corresponds to a ridge. Also, it will be understood that when the bone mineral density is decreased, a portion corresponding to a valley becomes wider and a portion corresponding to a mountain slope becomes more sharply inclined. Accordingly, the trabecular index becomes smaller as the decalcification of bone proceeds.

At step 40, an actual bone mineral density of the distal radius is estimated using the functional relation between the trabecular index and the bone mineral density of the distal radius.

Figure 4:
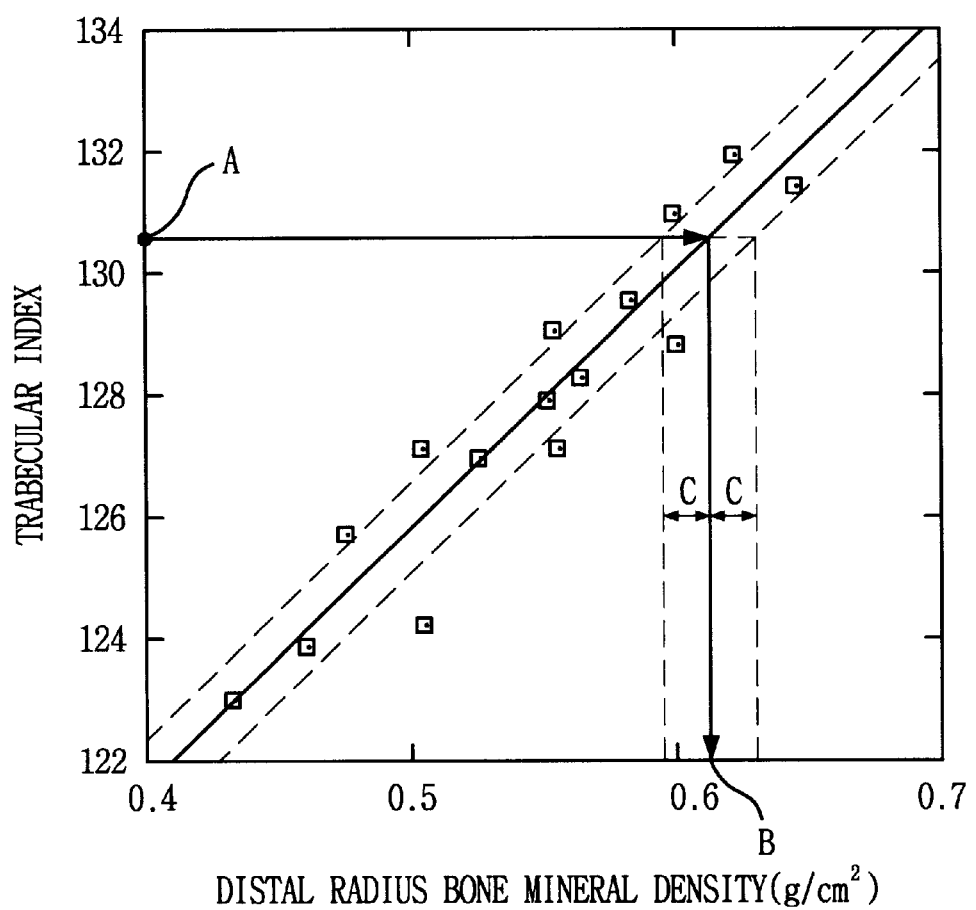
FIG. 4 is a graph illustrating a relation between a trabecular index and a quantitative bone mineral density of a distal radius.

At step 41, two-dimensional data of sampled trabecular indices and sampled bone mineral densities are obtained from the sufficient number of distal radius samples. The sampled trabecular indices are obtained using the procedure of the steps 10 to 34. The sampled bone mineral densities are measured by a dual energy X-ray absorptiometry (a bone densitometer). The sampled trabecular indices and the sampled bone mineral densities are employed in a graph of FIG. 4. The x-axis of the graph denotes the distal radius bone mineral density measured by the dual energy X-ray absorptiometry and the y-axis of the graph denotes the trabecular index on the distal radius X-ray image. Then, the linear functional relation between the trabecular index and the bone mineral density is obtained by the linear regression. For example, the linear functional relation obtained by the linear regression is illustrated by an oblique solid line in FIG. 4. In order to illustrate the statistical deviation of the data from the linear regression line, two dotted lines are positioned on the right and left of the oblique solid line, respectively. The horizontal distance between the dotted line and the solid line is equal to the average distance between the linear regression line and the two-dimensional data in the horizontal direction.

At step 42, when the trabecular index of the distal radius is given, the actual bone mineral density corresponding to the given trabecular index is estimated using the linear regression line. For example, when the trabecular index ("A" in FIG. 4) is obtained in the distal radius X-ray image, corresponding bone mineral density ("B" in FIG. 4) is estimated using the linear regression line. The statistical deviation of the estimated bone mineral density is determined by a horizontal distance ("C" in FIG. 4).

Particularly, the values and images described in the present invention may be varied for the sake of performance improvement of the present invention. As described above, the method for obtaining the trabecular index analyzes the trabecular pattern displayed on the X-ray image and quantifies the trabecular patterns changes due to decalcification of trabeculae, thereby obtaining the trabecular index. The method for estimating the bone mineral density obtains the trabecular indices and then estimates the bone mineral density corresponding to the trabecular index using the linear functional relation between the trabecular index and the bone mineral density.

In accordance with another embodiment of the present invention, the method for obtaining the trabecular index and estimating the bone mineral density can be implemented by using a calcaneus, a mandible, and so on instead of the distal radius.

Although the preferred embodiment of the invention has been disclosed for illustrative purpose, those skilled in the art will appreciate that various modifications, additions and substitutions are possible, without departing from the scope and spirit of the invention as disclosed in the accompanying claims.

What is claimed is:

1. A method for obtaining a trabecular index using a trabecular pattern in a computer, comprising the steps of:
   (a) obtaining an X-ray image of a bone;
   (b) determining a region of interest on the X-ray image;
   (c) dividing the region of interest into a plurality of blocks including a plurality of pixels;
   (d) calculating a gray level of each pixel;
   (e) scaling gray levels of the pixels for each block with a linear function;
   (f) calculating an average gray level of each block; and
   (g) obtaining the trabecular index by re-averaging the average gray levels for the blocks.

2. The method as recited in claim 1, wherein the step (b) includes, the steps of:
   (b1) determining the region of interest as a square; and
   (b2) aligning one side of the square with the direction of trabecular lines of the X-ray image.

3. The method as recited in claim 1, wherein each block has a side of length corresponding to an average distance between trabecular lines displayed on the X-ray image of the bone, and the direction of each block is the same as that of the region of interest.

4. The method as recited in claim 1, wherein the step (e) includes the step of scaling the gray levels of each block with the linear function such that the highest and lowest gray levels have predetermined constant values.

5. The method as recited in claim 1, wherein the bone is a distal radius.

6. The method as recited in claim 1, wherein the bone is a calcaneus.

7. The method as recited in claim 1, wherein the bone is a mandible.

8. A method for estimating a target bone mineral density using a target trabecular index in a computer, comprising the steps of:
   (a) obtaining X-ray images of sample bones;
   (b) determining regions of interest on the X-ray images;
   (c) obtaining a trabecular index corresponding to each region of interest;
   (d) measuring a bone mineral density of each sample with a bone densitometer;
   (e) obtaining a functional relation between the trabecular index and the bone mineral density; and
   (f) estimating the target bone mineral density using the target trabecular index related to a target bone from the functional relation wherein the step (c) includes the steps of:
      (c1) dividing said each region of interest into a plurality of blocks, each block containing a multiplicity of pixels;
      (c2) calculating a gray level of each pixel;
      (c3) scaling gray levels of the pixels for each block with a linear function;
      (c4) calculating an average gray level of said each block; and
      (c5) obtaining the trabecular index by re-averaging the average gray levels of the blocks of said each region of interest.

9. The method as recited in claim 8, wherein the step (b) includes, the steps of:
   (b1) determining each region of interest as a square; and
   (b2) aligning one side of the square with the direction of trabecular lines of each X-ray image.

10. The method as recited in claim 8, wherein the step (c) includes, the steps of;
    (c1) dividing each region of interest into a plurality of blocks including plurality of pixels;
    (c2) calculating a gray level of each pixel;
    (c3) scaling gray levels of the pixels for each block with a linear function;
    (c4) calculating an average gray level of each block; and
    (c5) obtaining the trabecular index by re-averaging the average gray levels for the blocks.

11. The method as recited in claim 8, wherein the step (e) includes the step of obtaining a linear functional relation between the trabecular index and the bone mineral density by a linear regression.

12. The method as recited in claim 8, wherein the step (f) includes, the steps of;
    (f1) obtaining a target X-ray image of the target bone;
    (f2) determining a target region of interest on the target X-ray image;
    (f3) obtaining the target trabecular index corresponding to the target region of interest: and
    (f4) estimating the target bone mineral density related to the target trabecular index of the target bone from the functional relation.

13. The method as recited in claim 8, wherein each block has a side of length corresponding to an average distance between trabecular lines displayed on the X-ray image of the bone, and the direction of each block is the same as that of the region of interest.

14. The method as recited in claim 8, wherein the step (c3) comprises the step of scaling the gray levels of each block with the linear function such that the highest and lowest gray levels have predetermined constant values.

15. The method as recited in claim 8, wherein the sample bone is a distal radius.

16. The method as recited in claim 8, wherein the sample bone is a calcaneus.

17. The method as recited in claim 8, wherein the sample bone is a mandible.

18. A computer-readable medium for performing the steps of:
   (a) obtaining an X-ray image of a bone;
   (b) determining a region of interest on the X-ray image;
   (c) dividing the region of interest into a plurality of blocks including a plurality of pixels;
   (d) calculating a gray level of each pixel;
   (e) scaling gray levels of the pixels for each block with a linear function;
   (f) calculating an average gray level of each block; and
   (g) obtaining the trabecular index by re-averaging the average gray levels for the blocks.

19. A computer-readable medium for performing the steps of
   (a) obtaining X-ray images of sample bones;
   (b) determining regions of interest on the X-ray images;
   (c) obtaining a trabecular index corresponding to each region of interest;
   (d) measuring a bone mineral density of each sample with a bone densitometer;
   (e) obtaining a functional relation between the trabecular index and the bone mineral density; and
   (e) estimating a target bone mineral density using a target trabecular index related to a target bone from the functional relation wherein the step (c) includes the steps of:
   (c1) dividing said each region of interest into a plurality of blocks, each block containing a multiplicity of pixels;
   (c2) calculating a gray level of each pixel;
   (c3) scaling gray levels of the pixels for each block with a linear function;
   (c4) calculating an average gray level of said each block; and
   (c5) obtaining the trabecular index by re-averaging the average gray levels of the blocks of said each region of interest.

20. The method as recited in claim 19, wherein the step (f) includes, the steps of;
   (f1) obtaining a target X-ray image of the target bone;
   (f2) determining a target region of interest on the target X-ray image;
   (f3) obtaining. the target trabecular index corresponding to the target region of interest: and
   (f4) estimating the target bone mineral density related to the target trabecular index of the target bone from the functional relation.

* * * * *